United States Patent
Fine et al.

(10) Patent No.: US 6,758,214 B2
(45) Date of Patent: Jul. 6, 2004

(54) SIMPLE NITRIC OXIDE GENERATOR FOR AMBULATORY AND/OR BEDSIDE INHALED NO TREATMENT

(75) Inventors: David H. Fine, Lincoln, MA (US); Freeman W. Fraim, Lexington, MA (US); George Jarvis, Arlington, MA (US)

(73) Assignee: CyTerra Corporation, Waltham, MA (US)

( * ) Notice: Subject to any disclaimer, the term of this patent is extended or adjusted under 35 U.S.C. 154(b) by 393 days.

(21) Appl. No.: 09/769,766

(22) Filed: Jan. 26, 2001

(65) Prior Publication Data

US 2001/0037810 A1 Nov. 8, 2001

Related U.S. Application Data

(60) Provisional application No. 60/178,693, filed on Jan. 28, 2000.

(51) Int. Cl.[7] ............................................. A61M 16/00
(52) U.S. Cl. ..................................... 128/203.12; 45/56
(58) Field of Search ......................... 128/203.12; 95/56, 95/153, 154; 423/403

(56) References Cited

U.S. PATENT DOCUMENTS

| | | | |
|---|---|---|---|
| 5,396,882 A | 3/1995 | Zapol | |
| 5,485,827 A | 1/1996 | Zapol et al. | |
| 5,692,495 A | 12/1997 | Sheu | |

OTHER PUBLICATIONS

English Abstract.
Hirokazu Tsukahara, et al. "Gas–Phase Odidation of Nitric Oxide: Chemical Kinetics and Rate Constant", Nitric Oxide: Biology and Chemistry, vol. 3, No. 3, pp. 191–198 (1998).

Jesse D. Roberts Jr, et al., "Inhaled Nitric Oxide", Seminars in Perinatology, vol. 24 No. 1, pp. 55–58, (Feb., 2000).

Pulmonox Medical Inc., "The Company", About Pulmonox.

Scott Medical Products, "Special Applications".

INO Therapeutics, INOmax

Gregory M. Sokol., "Nitrogen Dioxide Formation during Inhaled Nitric Oxide Therapy", Clinical Chemistry, pp382–387, 1999.

Francoe M, et al., "Inhaled nitric oxide: technical aspects of administration and monitoring", National Library of Medicine, Crit Care Med, pp. 782–96.

David H. Fine, "Critical Evaluation of Saltmaz Technique for NO, Analysis in the 0–100 Ppm Range", Fuels Research Laboratory, pp. 348–350 (1972).

Martin Franco, et al., "Inhaled nitric oxide: Technical aspects of administration and monitoring", Crit Car Med, vol. 26, pp. 782–796 (1998).

NitroMed–Business Rationale, "Company".

Primary Examiner—Henry Bennett
(74) Attorney, Agent, or Firm—Fish & Richardson P.C.

(57) ABSTRACT

A nitric oxide delivery system for delivering nitric oxide to a patient to treat a medical condition includes a container, a nitric oxide generation chamber, and a pump. The container is designed to contain a nitrogen-containing compound. The nitric oxide generation chamber includes a heat source and is designed to generate nitric oxide from the nitrogen-containing compound. The pump is designed to transfer at least a part of the nitrogen-containing compound from the container to the nitric oxide generation chamber.

31 Claims, 4 Drawing Sheets

SIMPLE NITRIC OXIDE GENERATOR FOR AMBULATORY AND/OR BEDSIDE INHALED NO TREATMENT

PRIOR APPLICATIONS

This application claims priority from U.S. Provisional Application No. 60/178,693, which was filed on Jan. 28, 2000, and which is incorporated herein by reference in its entirety.

TECHNICAL FIELD

This invention relates to generation of nitric oxide, and more particularly to the generation of nitric oxide for delivery to a patient.

BACKGROUND

Nitric oxide ("NO") gas, also known as a nitrosyl radical, is a free radical that is an important signaling molecule in pulmonary vessels. Its importance was first recognized by Robert Furchgott who discovered that the Endothelium-derived Relaxing Factor ("EDRF"), a naturally occurring chemical produced by the endothelium cell lining of blood vessels from oxygen and the amino acid, L-arginine, was identical to NO. The NO diffuses into smooth muscle cells in the vascular wall and causes dilation of the blood vessel's wall ("vasodilation").

NO that diffuses into the blood vessel displaces oxygen from hemoglobin, to form methemoglobin. The bright red methemoglobin does not play a role in vasodilation.

Inhaling low levels of NO, such as in range of between 1 to 100 parts per million ("ppm"), rapidly and safely decreases pulmonary artery hypertension in many patients without causing systemic hypotension. This result occurs without causing systemic hypotension because inhaled NO only dilates those pulmonary vessels that perfuse well-ventilated lungs. As a result, pulmonary gas exchange is improved while pulmonary vascular resistance is reduced and pulmonary blood flow is increased. In hypoxemic newborns with pulmonary hypertension, clinical studies have shown that delivering inhaled NO increases systemic oxygen levels and lessens the likelihood of extracorporeal membrane oxygenation.

Nitric oxide has also been observed to regulate cell proliferation. Recent studies suggest that inhaled NO selectively modulates the pulmonary artery's cellular proliferative response that is associated with lung injury. These recent studies also indicate that inhaled NO can be applied to attenuate or prevent pulmonary artery disease in patients with injured lungs.

Nitric oxide plays an active and direct role during infection by protecting the host and destroying the microbe causing the infection. For example, an overproduction of NO during septic shock has been described as potentially being responsible for the systemic vasodilation that can occur during septic shock.

Nitric oxide also may be used as an anticoagulant if delivered to the blood. Trace amounts of NO administered to the blood function as a platelet inhibitor to reduce platelet activation. Therapeutic levels of NO may prove useful for chronic anti-platelet therapy for patients with implanted mechanical valves. Moreover, while NO has a fundamental role in the control of blood pressure and micro-vascular motility and aiding in killing foreign invaders in the immune response, as described above, it also is the final common mediator in penile erection, for example, as the basis of the drug Viagra. It also is believed to play a major factor in the mechanisms of long-term memory.

Indigenous NO, measured in exhaled breath, can be used as the basis for a diagnostic or monitoring test. For example, exhaled NO can be used as a non-invasive means of monitoring inflammation of the upper and lower respiratory tract. In the normal upper airways, the bulk of exhaled NO originates from the paranasal sinuses. Exhaled NO is increased by nasal allergies and asthmatic airways. Exhaled NO is decreased by cystic fibrosis, nasal polyposis, and chronic sinusitis.

Conventional NO therapy includes delivering a stream of high concentration NO gas and a stream of air, oxygen, or nitrogen, and combining the streams immediately before delivering the NO to the patient to provide NO to the patient at a therapeutic level of less than 100 ppm. The need to combine the streams immediately before delivery to the patient is a consequence of the reaction kinetics of NO with oxygen to preferentially produce nitrogen dioxide at ambient temperature, which then may be converted in the presence of water to nitric acid and nitrous acid, which are detrimental to a patient's lungs.

Nitric oxide gas typically is stored in glass or metal containers or bottles at a high concentration, e.g., 800 ppm, in an oxygen-free environment. The inner surface of a container is polished or deactivated to prevent adsorption of NO on the walls of the container.

There are two reasons for the concentration in the container being eight to ten times higher than therapeutic levels. First, NO must be stored in an oxygen-free environment, such as a nitrogen environment. Accordingly, to provide 100 ppm of NO in air or oxygen, the NO and nitrogen stream of gas must be mixed and diluted with air or oxygen immediately before use. Second, gas bottles are expensive and cumbersome to transport, such that supplying the NO at a high concentration and having the user dilute the NO to a low concentration reduces the cost of otherwise supplying NO at a therapeutic level.

SUMMARY

In one general aspect, a nitric oxide generation and delivery system for delivering nitric oxide to a patient to treat a medical condition includes a container, a nitric oxide generation chamber, and a pump. The container is configured to contain a nitrogen-containing compound. The nitric oxide generation chamber includes a heat source and is configured to generate nitric oxide from the nitrogen-containing compound. The pump is configured to transfer at least a part of the nitrogen-containing compound in the container to the nitric oxide generation chamber.

Implementations may include one or more of the following. For example, the medical condition may include vasoconstriction. The system may include a filter system that filters impurities from the nitric oxide, a cooling system that cools the nitric oxide, a monitoring system that monitors a concentration of nitric oxide and/or nitrogen dioxide, and a breathing tube connectable to the patient to deliver the nitric oxide to the patient.

The system also may include a control system that controls an operation of the pump to transfer the nitrogen-containing compound in the container to the nitric oxide generation chamber. The control system may control the operation of the pump to transfer the nitrogen-containing compound based on a signal received from a monitoring system that monitors a concentration of nitric oxide.

The nitrogen-containing compound may include ammonia. The nitrogen-containing compound and/or the ammonia may be in the form of solid, a gas, and/or a liquid.

The container may include a heater and/or a metering valve. The NO generation chamber may include a catalyst, such as nickel and/or a noble metal, and the catalyst may be heated.

The controller may control the operation of the pump to transfer the nitrogen-containing compound in the container to the nitric oxide generation chamber such that a therapeutic dose of nitric oxide is generated in the nitric oxide generation chamber. The therapeutic dose of the nitric oxide may be between approximately 1 ppm and 100 ppm nitric oxide, and more particularly, between approximately 20 ppm and 80 ppm nitric oxide. The container may include a container release mechanism that is configured to release the compound into a line such that the pump can pass a gas through the line to transfer the compound to the nitric oxide generation chamber. The container release mechanism may be one of a metered valve, a heater, or a variable diameter opening. The gas may be oxygen or air.

In another general aspect, treating a patient having a medical condition by using nitric oxide gas includes providing a stream of gas that includes a nitrogen-containing compound, reacting the nitrogen-containing compound in a nitric oxide generation chamber to produce a stream of gas that includes nitric oxide, and delivering the stream of gas that includes nitric oxide from the nitric oxide generation chamber to the patient. The nitric oxide generation and delivery system provides considerable advantages. For example, the system generates NO gas at the concentration at which the NO gas will be delivered to the patient, and immediately delivers the NO gas to the patient. Moreover, the system generates NO gas at a location near the patient. Thus, there is a drastic reduction in the quantity of nitrogen dioxide that will be produced between the time the NO is generated and the time at which the NO reaches the patient because that time is short.

The system also does not involve multiple gas canisters and mixing equipment, which are burdensome to move and potentially dangerous. Instead, the system is portable and, for example, can be used beside the bed, attached to a wheel chair, in an ambulatory harness, or under any conditions as dictated by each patient's individual situation.

Other features and advantages will be apparent from the description, the drawings, and the claims.

DESCRIPTION OF DRAWINGS

Like reference symbols in the various drawings indicate like elements.

DETAILED DESCRIPTION

At high temperatures, the thermodynamically stable oxide of nitrogen is nitric oxide ("NO") and, at ambient temperatures, the thermodynamically stable oxide of nitrogen is nitrogen dioxide ("NO$_2$"). Nitrogen dioxide gas is hazardous to humans because it dissolves in water to form nitrous acid. Nitrogen dioxide can further react in the gas phase with NO or itself to form N$_2$O$_3$ and N$_2$O$_4$, which also dissolve in water to form nitric acid and nitrous acid. The formation of even small amounts of either nitric acid or nitrous acid in a lung can be fatal. More particularly, the Occupational Safety and Health Administration ("OSHA") has set a maximum exposure level to NO$_2$ of 5 parts per million ("ppm"). Thus, the delivery of NO to a patient by inhalation for a therapeutic use is constrained by the concern that NO at ambient temperatures forms nitrogen dioxide, and that the nitrogen dioxide may form nitric acid in the lungs.

The oxidation of NO with oxygen to form NO$_2$ occurs by means of the following homogenous three-body reaction, with a reverse temperature coefficient (i.e., the reaction speed increases with decreasing temperature):

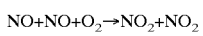

$$NO+NO+O_2 \rightarrow NO_2+NO_2$$

Figure 1:
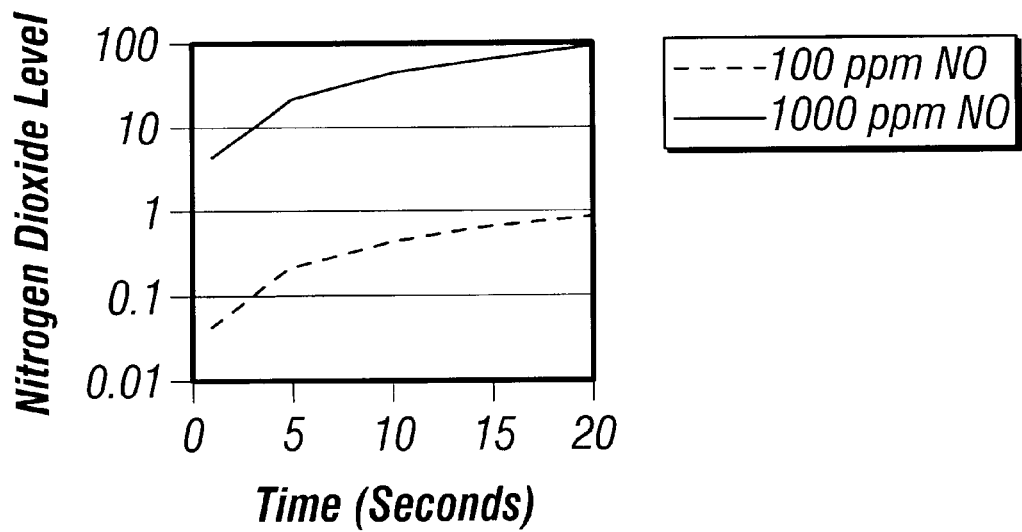
FIG. 1 is a graphic showing the impact of nitric oxide level on nitrogen dioxide formation.

Thus, for the reaction to proceed, two molecules of NO and one molecule of oxygen need to be in contact with each other at the same time. This becomes more and more difficult as the concentration of NO is reduced. The rate of formation of NO$_2$ is proportional to the square power of the NO concentration and the single power of the oxygen concentration. Consequently, reducing the NO concentration by a factor of ten, reduces the amount of NO$_2$ formed in a given time by a factor of one hundred. A graphical example of this type of reduction is shown in FIG. 1 below.

The ability to reduce the NO$_2$ formation and concentration in a delivered gas based on the effect of the square power of the NO concentration provides a basis for a system for delivering therapeutic amounts of NO to a patient with a much reduced likelihood of nitric acid formation. For example, since therapeutic levels of inhaled NO are in the 1 to 100 ppm range, and more particularly in the 20 to 80 ppm range, with levels above 100 ppm being potentially hazardous to the patient, using concentrations above 100 ppm should be avoided for at least two reasons. First, concentrations of NO above 100 ppm can have deleterious effects on patients. Second, because the formation of NO$_2$ occurs at a rate that is proportional to the square power of the NO concentration, reducing the NO concentration ultimately reduces the amount of nitrogen dioxide formed. However, as described above, conventional NO therapy relies on the opposite by providing high concentrations of NO that then must be diluted to a therapeutic level.

Figure 2:
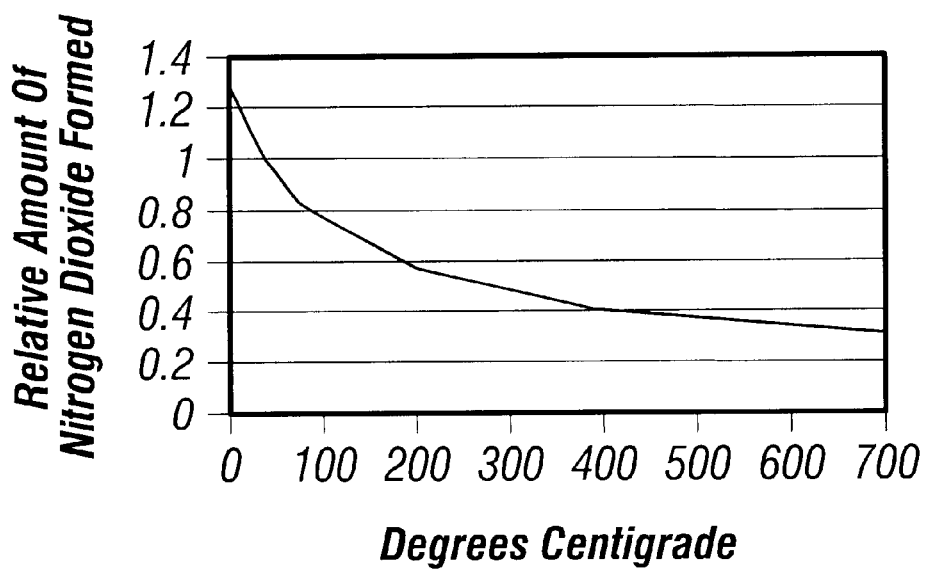
FIG. 2 is a graphic showing the effect of temperature on the amount of nitrogen dioxide formed.

There also is a temperature factor in the formation of NO$_2$: the formation of NO$_2$ is favored by low temperatures, although this temperature dependence is relatively weak. FIG. 2 is a graphical representation of the formation of NO$_2$ from NO that is normalized to 37° C. The rate is 10% faster at 25° C. than at 37° C., but is slower at higher temperatures. For example, at 700° C., only a third of the NO$_2$ would be formed as compared to 37° C.

To generally avoid the problem of NO being oxidized to NO$_2$ during mixing and dilution, the mixing and dilution steps should be eliminated by providing the NO at the desired concentration for inhalation. This can be accomplished by providing the NO at the desired concentration in a tank or by synthesizing the NO at the desired concentration in the stream of air in which the NO is delivered to the patient.

Figure 3:
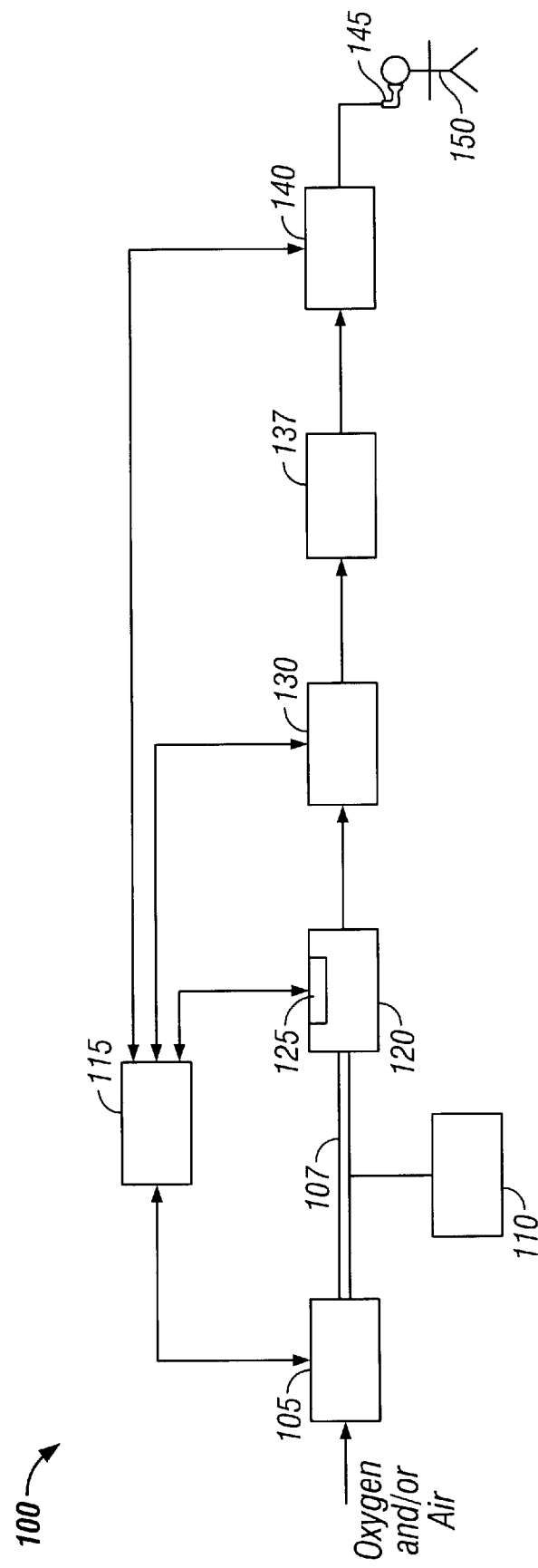
FIG. 3 is a plan view of a nitric oxide generation and delivery system.

Referring to FIG. 3, a NO generation and delivery system 100 for producing a stream of NO includes a pump 105, a line 107, a container 110, a controller 115, a NO generation chamber 120, a heating element 125, a filter system 130, a cooling system 137, a monitor 140, and a breathing tube 145. The breathing tube 145 is connectable to a patient 150.

The controller 115 controls the speed of the pump 105, the temperature and amount of heat generated by the heating element 125, and the operation of the filter system 130, and monitors the signals produced by the monitor 140. The controller 115 can control the pump velocity of the air flow through the line to control air flow to the patient.

The filter system 130 filters impurities from the stream of gas produced in the NO generation chamber 120. For example, the filter system 130 can use conventional techniques to filter organic fragments from the stream of gas, if desired or necessary.

The cooling system 137 cools the stream of gas, if necessary, from the temperature in the NO generation chamber to a temperature at which the stream of gas can be inhaled safely by the patient.

The monitor 140 monitors the concentration of NO in the stream of gas. The monitor also may detect or monitor the concentration of $NO_2$ in the gas, if necessary, and may provide a warning if the NO concentration is outside of a set range or if the concentration of $NO_2$ is above a set value. Examples of monitoring techniques include chemiluminescence and electrochemistry, and are discussed in *Inhaled nitric oxide: Technical aspects of administration and monitoring*, Martin Francoe et al, as published in *Critical Care Medicine*, Volume 26, number 4 (1998), which is incorporated herein by reference in its entirety.

The controller 115 can use the monitored values to control the speed of the pump and the temperature in the NO generation chamber to control the NO concentration delivered to the patient. For example, the controller 115 can be set to deliver a therapeutic dose of inhalation NO that is generated and delivered at that dose concentration without the extra step of diluting the NO with another gas.

Figure 4:
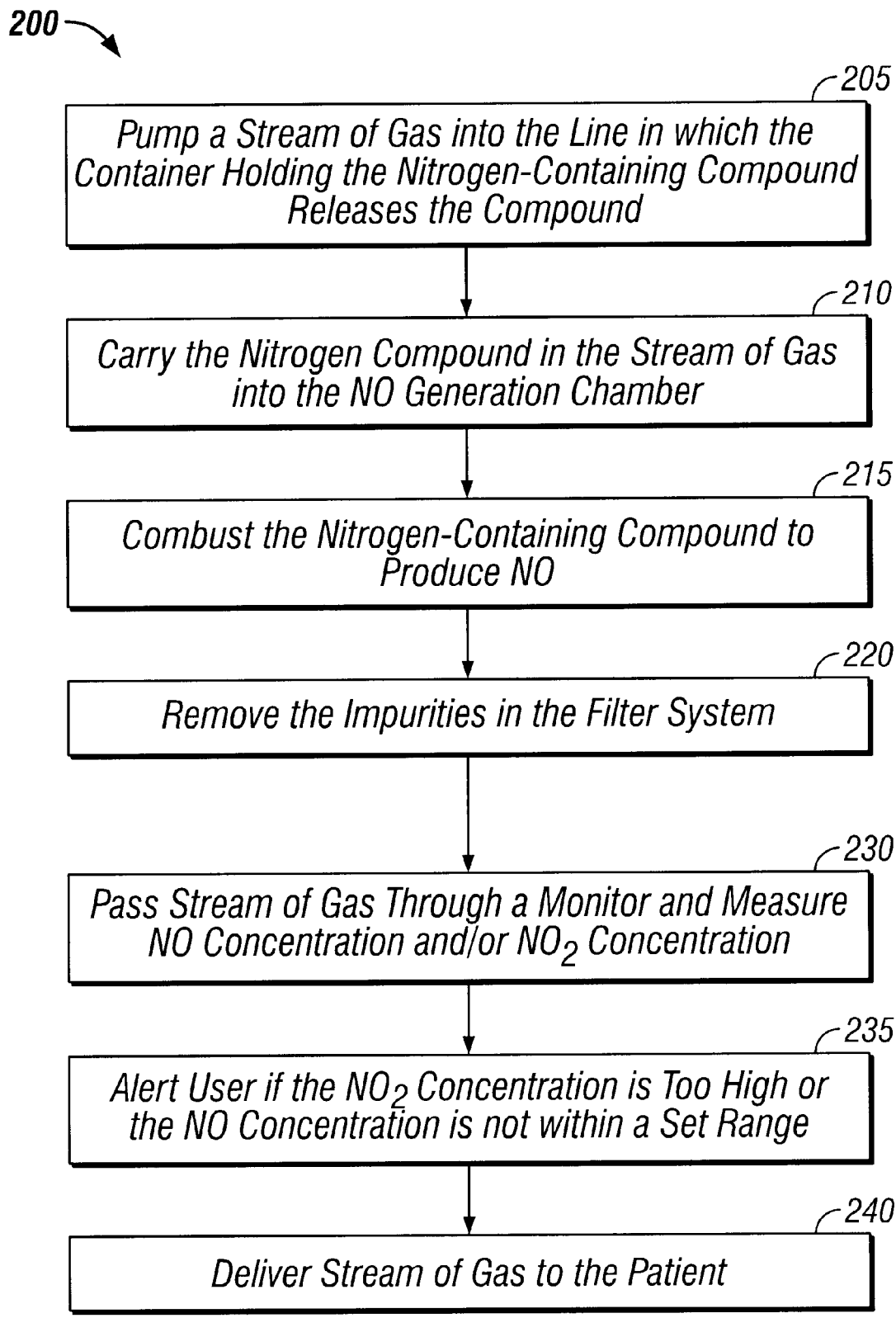
FIG. 4 is a flow chart of a nitric oxide generation and delivery process.

Referring also to FIG. 4, in a general process for generating a stream of NO 200, the pump 105 pumps or otherwise conveys air and/or oxygen as a stream of gas into and through the line 107 to which the container 110 is attached and into which the nitrogen containing compound is released from the container (step 205). The container 110 holds the nitrogen containing compound that can be used to form NO gas. The compound can be in the form of a solid, liquid, or gas, and the container 110 includes a release mechanism that is suitable for releasing the compound into the line 107 from the container. For example, the release mechanism can be a metered valve, a heater, or a variable diameter opening that is controllable to release the compound into the line 107. The stream of gas carries the nitrogen containing compound released into the line 107 from the container 110 into the NO generation chamber 120 (step 210). The speed of the pump is variable and controlled by the controller 115 to control the amount of nitrogen containing compound that is carried in the gas. The heating element 125 in the NO generation chamber heats the NO generation chamber to a sufficient temperature to combust or pyrolyze the compound to produce NO gas (step 215). The stream of gas then passes into and through the filter system 130 to remove impurities, if any (step 220). In general, the amount of the nitrogen containing compound that is provided is controlled to provide the necessary dosage to the patient. Moreover, the reaction conditions in the NO generation chamber are controlled to ensure complete, or almost complete, reaction so that no impurities are formed.

The gas passes from the filter system into and through the monitor 140 which, if necessary, measures the concentration of NO and/or $NO_2$, if necessary, are measured (step 230). Again, because the concentration of NO generated will be less than 100 ppm, based on nitric oxide's reaction kinetics, it is unlikely that nitrogen dioxide will be formed and present in relevant or harmful concentrations. If the $NO_2$ concentration is nonetheless monitored, the monitor can be configured to alert a user if the nitrogen dioxide concentration moves above a set limit. The monitor also can be configured to alert the user if the NO concentration moves outside of a set range (step 235). The stream of gas then is delivered from the monitor to the patient through the breathing tube 145 to provide NO inhalation therapy (step 240).

The breathing tube 145 can be any device or implement that is used to provide the NO gas stream to the patient and typically is selected by the physician based on the patient's condition. For example, the breathing tube 145 can be in the form of a tight-fitting or a loose-fitting mask, an intubation tube, a nasal delivery tube, or a tube that generally directs the gas in the region around the patient's mouth and/or nose. On a related note, the NO gas can be delivered in 100% oxygen, in air (approximately 20% oxygen), or in any oxygen concentration within that range. Again, the concentration typically is selected by the physician based on the patient's needs and condition.

It is noteworthy that the system 100 is designed such that the gas is generated and delivered to the patient in a short period. This design reduces the likelihood that nitrogen dioxide will be formed in the short time and space that it takes for the NO gas to pass from the NO generation chamber to the patient. Moreover, by generating the NO at or near the desired therapeutic concentration, the reaction kinetics favor NO.

Various nitrogen-containing compounds can be used in the NO delivery system 100. Generally, these compounds include any organic compound that contains nitrogen, such as, for example, organic nitrogen compounds, including ammonia or ammonium; nitroso compounds including N-nitroso, O-nitroso, C-nitroso, and S-nitroso; and nitro compounds including those having an O—$NO_2$ bond (e.g., nitroglycerin and PETN), a N—$NO_2$ bond (e.g., nitramines), or a C—$NO_2$ bond (e.g., TNT). The primary requirement is that the organic nitrogen-containing compound must be convertible directly or indirectly into NO gas.

EXAMPLE 1

One suitable nitroso category includes nitrosamines. One nitrosamine that can be used in the system 100 to produce NO is diphenyl nitrosamine, which has a labile N—NO bond. To produce an inhalation dosage of NO gas, typically between approximately 1 ppm and 100 ppm, and more particularly between approximately 20 ppm and 80 ppm, the desired concentration of delivered, inhalation NO is set on the controller 115. The controller 115 has software or embedded hardware that uses the value of the desired NO concentration to determine an initial speed of the pump 105, which directly relates to the amount of diphenyl nitrosamine that after being released from the container 110 into the line, is carried from the line 107, into the NO generation chamber 120.

The pump 105 pumps air through the line 107 to mix the stream of air with the diphenyl nitrosamine that has been released from the container 110 into the line. The stream of air carriers some of the diphenyl nitrosamine into the NO generation chamber 120.

The software in the controller 115 also uses the desired NO concentration to determine the temperature to which the heating element 125 must heat the NO generation chamber 120. In this example, the temperature is set to approximately 200° Celsius or higher, and more particularly to a temperature range between approximately 220° Celsius and 400°

Celsius. Although temperature has an effect on the concentration of NO delivered to the patient, it is a minor effect in comparison to the effect of the pump flow rate. The temperature has a greater effect on the completeness of the combustion or pyrolysis of the diphenyl nitrosamine.

When the air and the diphenyl nitrosamine are in the chamber 120, the diphenyl nitrosamine is pyrolyzed or combusted to release gaseous NO and solid phenyl fragments, such as diphenyl amine. The nitroso compounds can be pyrolyzed using high temperature pyrolysis or low temperature pyrolysis.

The constant action of the pump 105 forces the stream of gas from the NO generation chamber 120 into the filter system 130 in which any impurities, are removed. For example, the filter system 130 and/or the NO generation chamber 120 can include an acidic microstructure to trap the diphenyl amine impurities produced in the pyrolysis reaction.

The stream of gas then passes through the monitor 140 and the concentration of NO and/or $NO_2$ are measured. If the NO concentration is less than the set NO concentration, the controller 115 increases the speed of the pump 105 by a programmed amount that is expected to increase the NO concentration to a desired level. Conversely, if the NO concentration is too high, the controller 115 slows the speed of the pump 105. If the monitor $NO_2$ concentration is above a set point, the controller may be programmed to take a number of steps ranging from activating an alarm to warn the operator to shutting down the machine if the $NO_2$ concentration is too high. The step or steps to be taken may vary based on the actual $NO_2$ level.

After passing through the monitor, the stream of gas reaches the patient 150 though the breathing tube 145. Importantly, the stream of gas contains NO at the concentration of NO desired for NO therapy and no dilution or mixing of the NO is required or necessary. As a specific example, to deliver 100 ppm NO to a patient at an airflow rate of three liters per minute, 140 mg per hour of diphenyl nitrosamine are consumed in the system 100. Although the nitroso compound described above is a N—NO compound, the reaction and procedure will be the same for an O-nitroso, a S-nitroso, and a C-nitroso compound.

EXAMPLE 2

Another suitable category of compounds to use in the system 100 to produce NO gas are nitro compounds, such as potassium nitrate, nitroglycerin, PETN, RDX, HMX, and TNT. The nitro compound is processed in the system 100 according to the process 200 as described above under conditions that are specific to the particular nitro compound used and with minor additions to the system 100. For example, the O—$NO_2$ and the N—$NO_2$ compounds decompose at approximately 400° Celsius, whereas the C—$NO_2$ compound decomposes at approximately 800° Celsius. The nitro compounds decompose to produce $NO_2$, which must be further decomposed to produce NO gas. This is accomplished by passing the $NO_2$ over a silver catalyst that may be positioned within the NO generation chamber 120 or in the line between the NO generation chamber and the filter system 130. As a specific example, to deliver 100 ppm NO to a patient at an airflow rate of three liters per minute, 60 mg per hour of potassium nitrate will be consumed in the system 100.

EXAMPLE 3

Organic nitrogen compounds contain a nitrogen atom and can be oxidized (or burned) in the gas phase in air or oxygen to quantitatively produce NO, $CO_2$, and $H_2O$. The reaction generally works best at approximately 800° Celsius over a nickel catalyst. There are millions of organic nitrogen-containing compounds that can be uses to generate NO in this method. Some of the factors to consider in the choice of the compound are stability, price, toxicity and availability. Ammonium compounds, such as ammonia, are one example of the class of organic nitrogen-containing compounds.

If an ammonium compound is used in the process 100, the container 110 can be configured to hold, for example, pure ammonia, ammonium hydroxide, ammonium carbonate, ammonium nitrate, or a solution of ammonia in water. These compounds are produced industrially in large quantities at low cost, and can be oxidized to produce NO with the only by-product being water and carbon dioxide. Another advantage of these ammonia compounds is that they are generally safe. In fact, ammonium salts are used medicinally as "smelling salts." The container 110 also can be constructed to function as a reservoir that receives a stream of an ammonium compound and water and controllably releases the stream into the line 107, and the controller 115 can be programmed to control the concentration of ammonia ("$NH_3$") in the solution in the container by varying the feed rates of the ammonium compound and the water into the container. The pump 105 uses air or oxygen to spray the ammonium compound in solution form onto a hot catalytic surface in the NO generation chamber 120 to oxidize the $NH_3$ to NO. Specifically, ammonia can be oxidized over a noble metal catalyst at about 1000° Celsius or over a nickel catalyst at about 800° Celsius to produce NO. The nickel can be in the form of an electrical element and can function as a catalyst when the $NH_3$ is sprayed onto it.

The amount of $NH_3$ solution supplied by the pump 105 and sprayed onto the surface is kept sufficiently small and controlled so that only the desired therapeutic level of NO is produced and delivered to the patient. Moreover, since the oxidation reaction occurs in the air or oxygen stream conveying the ammonia compound, no mixing or dilution of the NO gas produced is necessary, and the gas stream can be delivered to the patient after filtering, if necessary, in the filter system 130, and cooling in the cooling system 137. The controller 115 receives from the monitor 140 signals indicating the concentration of NO in the gas and controls the NO concentration in the air or oxygen stream by varying either the concentration of the $NH_3$ in the container 110, or by changing the flow rate of the pump 105. As a specific example, to deliver 100 ppm NO to a patient at an airflow rate of three liters per minute, 12 mg per hour of ammonia will be consumed in the system 100.

Figure 5:
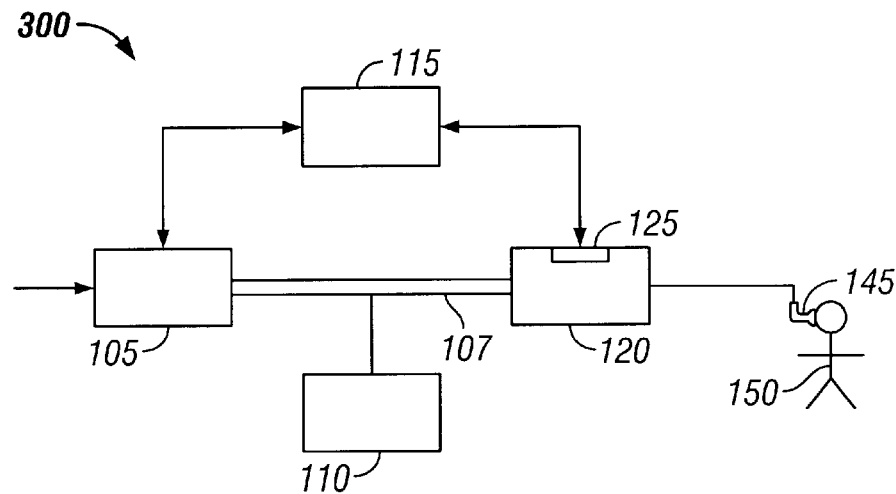
FIGS. 5–7 are plan views of other nitric oxide generation and delivery systems.

Various modifications of the system 100 described above are possible. For example, referring to FIG. 5, a system 300 can be constructed that includes the pump 105, the line 107, the container 110, the controller 115, the NO generation chamber 120, and the heating element 125. In such a configuration, the flow rate of the pump 105, the temperature created in the NO generation chamber 120, and the resulting concentration of NO generated are well-characterized, such that the quantity of NO generated at a pump flow rate and temperature in the NO generation chamber is known. Thus, to produce a set quantity of NO for delivery to a patient, the user activates the system and merely sets the desired NO concentration on the controller.

Figure 6:
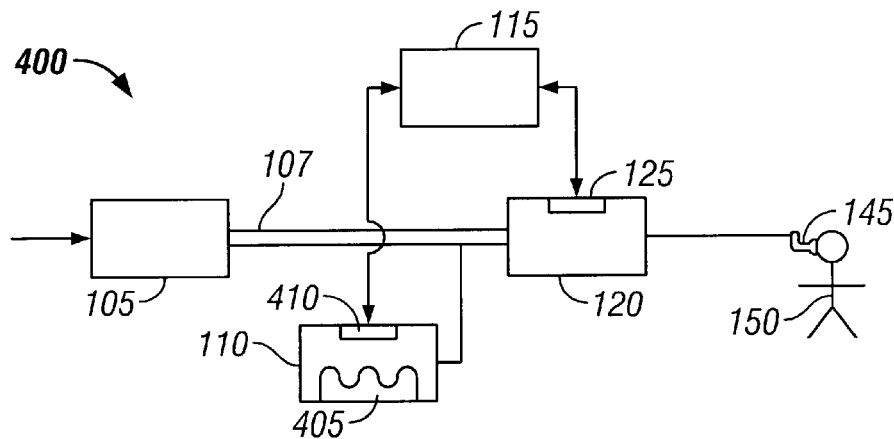

Referring to FIG. 6, a system 400 uses sublimation of a solid 405 in the container 110 to provide the compound that is oxidized to produce NO in the NO generation chamber 120. The solid 405 can be, for example, ammonia smelling salts, which sublimate to produce ammonia gas. When the ammonia gas enters the NO generation chamber in the stream of air and contacts the nickel or noble metal catalyst, the ammonia is oxidized to NO. By controlling the temperature in the container 110 using a heating system 410, the controller 115 can be programmed to control the rate at which the ammonia sublimates. For example, the controller 115 can be programmed with data correlating temperature with sublimation rate and sublimation rate with NO produced in the NO generation chamber such that the user can set a desired inhalation NO delivery dosage and the controller will control the temperature in the container 110 accordingly.

Figure 7:
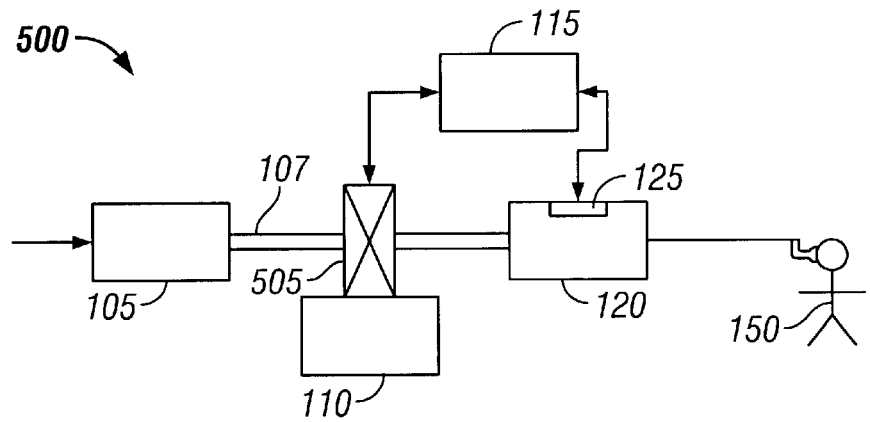

Referring to FIG. 7, a system 500 uses a pressurized gas in the container 110 to provide the compound that is oxidized to produce NO in the NO generation chamber 120. The pressurized gas can be, for example, ammonia gas. The container 110 includes a metering valve 505, whose operation is controlled by the controller 115, such that the release of the gas into the line 107 is controlled. The controller 115 may be programmed, for example, with a correlation between valve position and ammonia gas flow rate into the line 107. By controlling the flow rate of the ammonia gas and the air delivered by the pump 105, the controller is used to control the quantity of NO gas produced by the NO generation chamber 120.

Other embodiments are within the scope of the following claims. For example, the system 100 and method 200 can be used to treat any mammalian patient, including both humans and horses, both of which have been shown to respond to NO treatment.

What is claimed is:

1. A nitric oxide delivery system for delivering nitric oxide to a patient to treat a medical condition, the system comprising:
   a container configured to contain a nitrogen-containing compound;
   a nitric oxide generation chamber including a heat source and configured to generate nitric oxide from the nitrogen-containing compound; and
   a pump configured to transfer at least a part of the nitrogen-containing compound in the container to the nitric oxide generation chamber.

2. The nitric oxide delivery system of claim 1 further comprising a filter system positioned and configured to filter an impurity from the nitric oxide generated in the nitric oxide generation chamber.

3. The nitric oxide delivery system of claim 1 further comprising a cooling system positioned and configured to cool the nitric oxide generated in the nitric oxide generation chamber.

4. The nitric oxide delivery system of claim 1 further comprising a monitor system configured and positioned to monitor a concentration of nitric oxide and/or nitrogen dioxide output by the nitric oxide generation chamber.

5. The nitric oxide delivery system of claim 1 further comprising a control system configured to control a rate at which the pump transfers the nitrogen-containing compound in the container to the nitric oxide generation chamber.

6. The nitric oxide delivery system of claim 5 further comprising a monitor system configured and positioned to monitor a concentration of nitric oxide output by the nitric oxide generation chamber, wherein the control system is configured to control the operation of the pump to transfer the nitrogen-containing compound based on a nitric oxide concentration signal received from the monitor system.

7. The nitric oxide delivery system of claim 1 further comprising a breathing tube connectable to a patient and configured to deliver the nitric oxide to the patient.

8. The nitric oxide delivery system of claim 1 wherein the nitrogen-containing compound comprises ammonia.

9. The nitric oxide delivery system of claim 8 wherein the ammonia comprises a solid.

10. The nitric oxide delivery system of claim 8 wherein the ammonia comprises a gas.

11. The nitric oxide delivery system of claim 8 wherein the ammonia comprises a liquid.

12. The nitric oxide delivery system of claim 1 wherein the nitrogen-containing compound comprises a solid.

13. The nitric oxide delivery system of claim 1 wherein the nitrogen-containing compound comprises a gas.

14. The nitric oxide delivery system of claim 1 wherein the nitrogen-containing compound comprises a liquid.

15. The nitric oxide delivery system of claim 1 wherein the container includes a heater.

16. The nitric oxide delivery system of claim 1 wherein the container includes a metering valve.

17. The nitric oxide delivery system of claim 1 wherein the nitric oxide generation chamber include a catalyst.

18. The nitric oxide delivery system of claim 17 wherein the catalyst is heated.

19. The nitric oxide delivery system of claim 17 wherein the catalyst comprises nickel.

20. The nitric oxide delivery system of claim 17 wherein the catalyst comprises a noble metal.

21. The nitric oxide delivery system of claim 1 wherein the medical condition comprises vasoconstriction.

22. The nitric oxide delivery system of claim 5 wherein the controller controls the operation of the pump to transfer the nitrogen-containing compound in the container to the nitric oxide generation chamber such that a therapeutic dose of nitric oxide is generated in the nitric oxide generation chamber.

23. The nitric oxide delivery system of claim 22 wherein the therapeutic dose of nitric oxide comprises between approximately 1 ppm and 100 ppm nitric oxide.

24. The nitric oxide delivery system of claim 22 wherein the therapeutic dose of nitric oxide comprises between approximately 20 ppm and 80 ppm nitric oxide.

25. The nitric oxide delivery system of claim 22 wherein the container includes a container release mechanism that is configured to release the compound into a line and the pump passes a gas through the line to transfer the compound to the nitric oxide generation chamber.

26. The nitric oxide delivery system of claim 25 wherein the gas comprises oxygen.

27. The nitric oxide delivery system of claim 25 wherein the gas comprises air.

28. The nitric oxide delivery system of claim 25 wherein the container release mechanism comprises a metered valve.

29. The nitric oxide delivery system of claim 25 wherein the container release mechanism comprises a heater.

30. The nitric oxide delivery system of claim 1 wherein the patient is a human.

31. The nitric oxide delivery system of claim 1 wherein the patient is a horse.

* * * * *